(12) United States Patent
Ellman et al.

(10) Patent No.: US 7,427,295 B2
(45) Date of Patent: Sep. 23, 2008

(54) SPINAL FILL FOR DISK SURGERY

(75) Inventors: Alan G. Ellman, Oceanside, NY (US);
Jon C. Garito, Oceanside, NY (US)

(73) Assignee: Elli Quence, LLC, Oceanside, NY (US)

( * ) Notice: Subject to any disclaimer, the term of this patent is extended or adjusted under 35 U.S.C. 154(b) by 574 days.

(21) Appl. No.: 11/049,038

(22) Filed: Feb. 3, 2005

(65) Prior Publication Data

US 2006/0173464 A1    Aug. 3, 2006

(51) Int. Cl.
*A61F 2/44* (2006.01)
(52) U.S. Cl. .................... 623/17.16; 623/17.12
(58) Field of Classification Search ........................ None
See application file for complete search history.

(56) References Cited

U.S. PATENT DOCUMENTS 4,603,252 A  *  7/1986  Malek et al. ........... 250/227.14
6,428,576 B1     8/2002  Haldimann

FOREIGN PATENT DOCUMENTS

| WO | WO 0143625 | | 6/2001 |
|----|------------|---|--------|
| WO | WO 02/085262 | * | 10/2002 |
| WO | WO 02085262 | | 10/2002 |
| WO | WO 03020137 | | 3/2003 |
| WO | WO 03047472 | | 6/2003 |
| WO | WO 03099171 | | 12/2003 |
| WO | WO 2004073563 | | 9/2004 |

* cited by examiner

*Primary Examiner*—Corrine McDermott
*Assistant Examiner*—Christopher D Prone

(57) ABSTRACT

The invention is based on the use of polyisobutylmethacrylate instead of PMMA as an adhesive or spinal fill material for treating diseases of the spine. Polyisobutylmethacrylate has several advantages over PMMA, mainly less heat is developed during the in situ polymerization process. When using any spinal adhesive of fill material that is light activated, a tube can be used to transmit activating light to the light-activated adhesive or spinal polymerizable fill material at the surgical site. In addition, a mesh bag comprising optical fibers or similar light transmitting material can be employed to receive the injected light-activated fill, with the mesh bag, irradiated externally, for directing the light via the bag to the polymerizable fill.

8 Claims, 2 Drawing Sheets

SPINAL FILL FOR DISK SURGERY

BACKGROUND OF THE INVENTION

Our earlier filed patent application, Appl. Ser. No. 10/978096, filed 11/01/04, the contents of which are herein incorporated by reference, describes an electrosurgical instrument for removing intervertebral tissue for treating spinal ailments. Among the surgical procedures used for treating spinal ailments are cervical disc surgery (implant of another material as a substitute for a removed cervical disc), vertebroplasty with an adhesive for treatment of osteoporotic fractures, intervertebral disc prosthesis, and mechanical stabilizing of adjacent discs. Many of these procedures and other similar spinal treatments employ as the substitute adhesive material polymethylmethacrylate (PMMA) using in situ chemical activation or visible-light activation. However, adverse events during this procedure with this material may arise, namely, exothermal polymerization of the PMMA causing a temperature elevation high enough to possible lead to soft tissue or bone necrosis. This rise in temperature, which unavoidably accompanies the polymerization process, is exacerbated by the poor heat conduction of the vertebral anatomy. See, for example, "Temperature Elevation After Vertebroplasty With PMMA in the Goat Spine", by Verlaan et al., Journal of Biomedical Materials Research, 2003 Oct 15; 67B (1): 581-5.

SUMMARY OF THE INVENTION

An object of the invention is an improved surgical procedure for treating spine ailments involving the use of an adhesive or spinal polymerizable fill material whose temperature rise during polymerization is less than that of PMMA.

Another object of the invention is an improved instrument for introducing a light polymerizable adhesive or spinal fill material into spinal anatomy (disk or vertebrae) and that allows polymerizing light to be directly applied to the adhesive or spinal fill material to polymerize same.

A feature of the invention is based on the use of polyisobutylmethacrylate instead of PMMA as the adhesive or spinal fill material. Polyisobutylmethacrylate (herinafter "PIBMA") has several advantages over PMMA for the same purposes that PMMA has been used for surgical spinal procedures. The main advantage is that less heat, compared with PMMA, is developed during the in situ polymerization process, meaning less likelihood of causing soft tissue or bone necrosis. Moreover, the PIBMA material is just as easy to use and to handle for any of these spinal procedures as the PMMA. Further, the PIBMA is dimensionally stable, meaning that when it hardens it tends to retain its injected dimensions. Still further, X-Ray opaque materials, such as radio-opaque Ba or Sr compounds can be added so that the hardened material will be visible in an X-Ray or radiologic examination.

The instrument feature of the invention employs as the injecting tube or as an auxiliary tube tubular material that will transmit activating light to a light-activated adhesive or spinal polymerizable fill material at the surgical site. As a further feature, as an improvement on an existing procedure, a mesh bag comprising optical fibers or similar light transmitting material is employed to receive the injected light-activated fill, with the mesh bag, irradiated externally, for directing the light to the polymerizable fill. This has the advantage that the length of working time can be more readily controlled since the polymerization process when light activated can be more consistent. In this aspect of the invention, conventional light-cured polymethacrylate materials may be used, such as urethane dimethacrylate, as well as other non-methacrylate materials. The latter type of light-cured materials may even have a lower curing temperature than that of the PIBMA, and the advantages accompanying the use of light-curable resins will like the use of polyisobutylmethacrylate also be achieved.

The surgical procedures employing PIBMA can be the same as those using PMMA, except for the different fill material used and/or the use of light transmitting instruments or mesh bags.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF THE PREFERRED EMBODIMENTS

Figure 1:
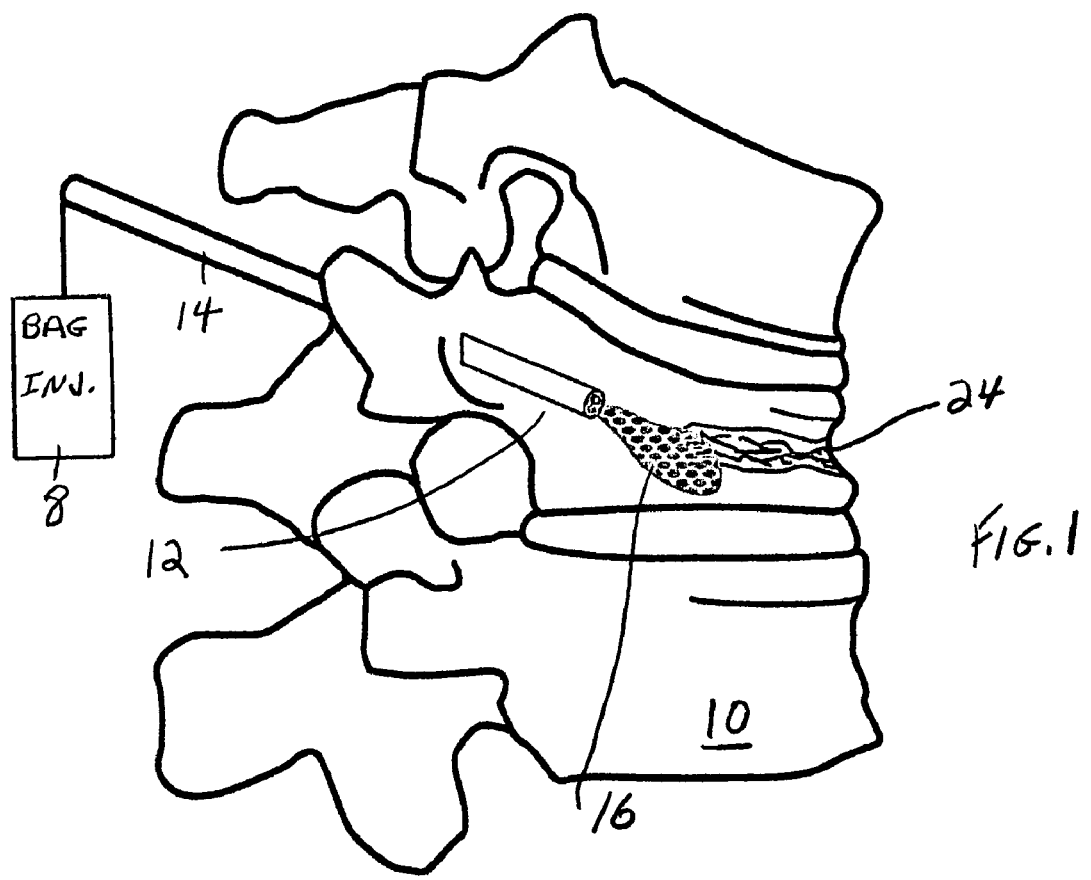
FIG. 1 schematically illustrates part of a spinal column with a cavity adjacent a tubular instrument.

The adhesive or spinal flowable polymerizable fill material according to a feature of the invention is PIBMA, polyisobutylmethacrylate. It is generally made up of two constituents that are mixed together by the surgeon outside of the surgical site to form a flowable paste or cream-like consistency that can be injected into the spinal tissue. The resultant cream is then injected into the spinal tissue at the surgical site. The material self-cures in situ in about 6-8 min. The first constituent is liquid monomer isobutylmethacrylate available commercially in liquid form. To it is added finely powered polyisobutylmethacrylate, a solid polymer. Typically, the liquid monomer is added to a suitable container, and sufficient powdered polymer added while mixing with, say, a spatula, until a creamy consistency is formed; the creamy mixture is then poured into the instrument for delivering the mixture, and then injected by the instrument into the spinal area at the surgical site. It begins to harden when exposed to air or liquid and generally sets hard, i.e. polymerizes, after about 6-8 minutes. When hardened it has similar or better properties than PMMA, including strength, retentive ability, and lack of distortion or low curing shrinkage, and importantly lower curing heat.

Light-cured plastic materials are also commercially available and include materials such as polyesters and acrylic materials, such as urethane dimethacrylate. Other well-known examples include the camphoroquinone/amine chemistry. Camphoroquinone features an absorption maximum in the visible spectrum at 470 nm (approximately blue light). In conjunction with a suitable amine, as is known, free radical species are generated to cause polymerisation and, therefore, hardening of the material. Polymerisation may be carried out using a suitable UV-generating lamp, such a quartz-halogen, plasma arc, or an argon laser.

With both kinds of adhesive or spinal polymerizable fill material a small amount of up to 20% of inert tissue-compatible non-toxic materials can be added to the mix. The inert material may be finely-divided glass, quartz, or ceramics. In addition, to make the hardened fill X-ray visible, a small amount of a known Ba or Sr X-ray opaque compound or material, such as $BaSO_4$ can be added to the mix.

The basic procedure is the same as used for other spinal procedures except for the spinal fill material used or the use of the light-activated fill. Essentially, a tubular member is inserted into the patient as in a conventional percutaneous or endoscopic procedure so that the distal end of the tubular member is at the spinal surgical site where the surgery is to be performed. Conventional instruments can be used to remove any degenerative material or portions of the disc nucleus or the disc itself as required by the selected procedure to form a cavity. Then, through the tube (or cannula as it is sometimes called) can be inserted again a conventional instrument for injecting a suitable spinal fill of adhesive material to fill up a crack in the vertebrae or to fill a cavity created in the nucleus, pulpous, or disc itself All of this can be done as is usual either by percutaneous or radiologic guidance under the view of an endoscopic camera to ensure that the injected fill material is positioned in the proper place. Following the teachings of the invention, the injected adhesive and fill material is the paste mixture of ingredients that will form the polyisobutyl-methacrylate when cured, or a paste mixture of ingredients that can be light-activated to harden. If the latter, then after the injection instrument has completed its task, it can be removed from the tubular member and a tubular member having the ability to transmit light inserted in its place. The light transmitting member may be a bundle of optical fibers, known in itself, the distal end of which is placed near the injected material and to the proximal end, outside the patient's body, is placed a source of UV radiation which travels through the fiber bundle and exits at the surgical site to illuminate the injected fill. If the fill is thick, it may be desirable to carry out this sequence in several small steps, meaning, that first a thin layer of the fill is injected, next the light-transmitting member is inserted to illuminate and cure the initial layer, then the sequence is repeated to form a second cured layer on top of the first cured layer, and so on until the cured fill has the desired size and volume.

If the known mesh bag procedure is used, then in an earlier step the mesh bag would be inserted in the cavity and the injection of fill material occur into the open end of the bag using again standard commercially-available instruments for this purpose. This would apply where the fill is the self-curing polyisobutylmethacrylate-forming mixture. Where the light-activated material is used, then as a further alternative the bag mesh can be composed of optical fiber strands so that the incident light is spread around the fill inside the bag by the optical fiber strands. The bag remains in place with the hardened fill.

As further alternative, instead of using an optical fiber bundle to transmit the light down the cannula, an additional tubular member with an internal mirrored surface can be inserted and the UV source coupled to the proximal end, such that the UV radiation is tranmitted down the tube by multiple reflections from the internal mirrored surface. The latter can be achieved in a conventional way by plating the inside of the tubular member with a thin layer of nickel as an example, or any other shiny material.

FIG. 1 schematically illustrates part of a spinal column 10 with a cavity 12 formed by any suitable instruments such as that described in the referenced patent application, and next to the cavity opening a tubular instrument 14 or cannula, again commercially-available, for injecting a previously-formed polymerizable fill into the cavity using the procedure described above. With the self-curing polymerizable PIBMA, nothing more is required until the fill sets.

Figure 4:
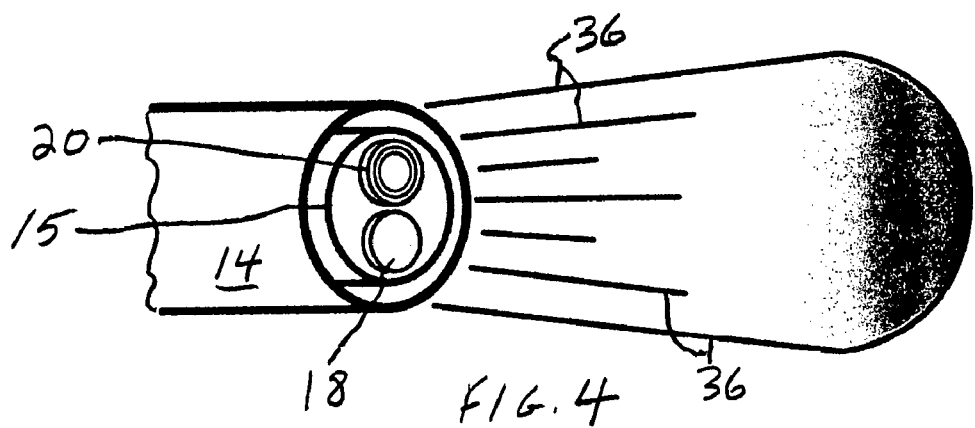
FIG. 4 schematically illustrates an enlarged view of the end of the injecting tube employed in a somewhat different manner.

FIG. 1 also schematically illustrates the part of a spinal column 10 into the cavity 12 of which a mesh bag 16 is shown being introduced in a known way and with the injecting tube 14 in place to inject a light-activated fill into the bag. In this use, it is preferred to employ a cannula 14 containing on its interior two side-by-side internal tubes 18, 20. The latter is illustrated in FIG. 4, in which the cannula 14 contains an inner tube 15 containing the two side-by-side internal tubes 18, 20. Between the inner 15 and outer tube 14 is an empty space 22, the purpose of which will be explained below. FIG. 1 illustrates that the lower tube 18 can be used to successively inject or administer the tubular mesh 16 and polymerizable fill. The adjacent upper tube 18 can be used for manipulating a guide bar or rod (not shown) to direct the bag to the position desired. Or alternatively, the adjacent upper tube 18 can be used with a viewer for viewing the site during the procedure. In the case illustrated, a spinal tissue has a fracture 24 around which a cavity has been formed and the mesh bag 16 injected from a suitable source 8 is positioned in the cavity alongside the fracture 24.

Figure 2:
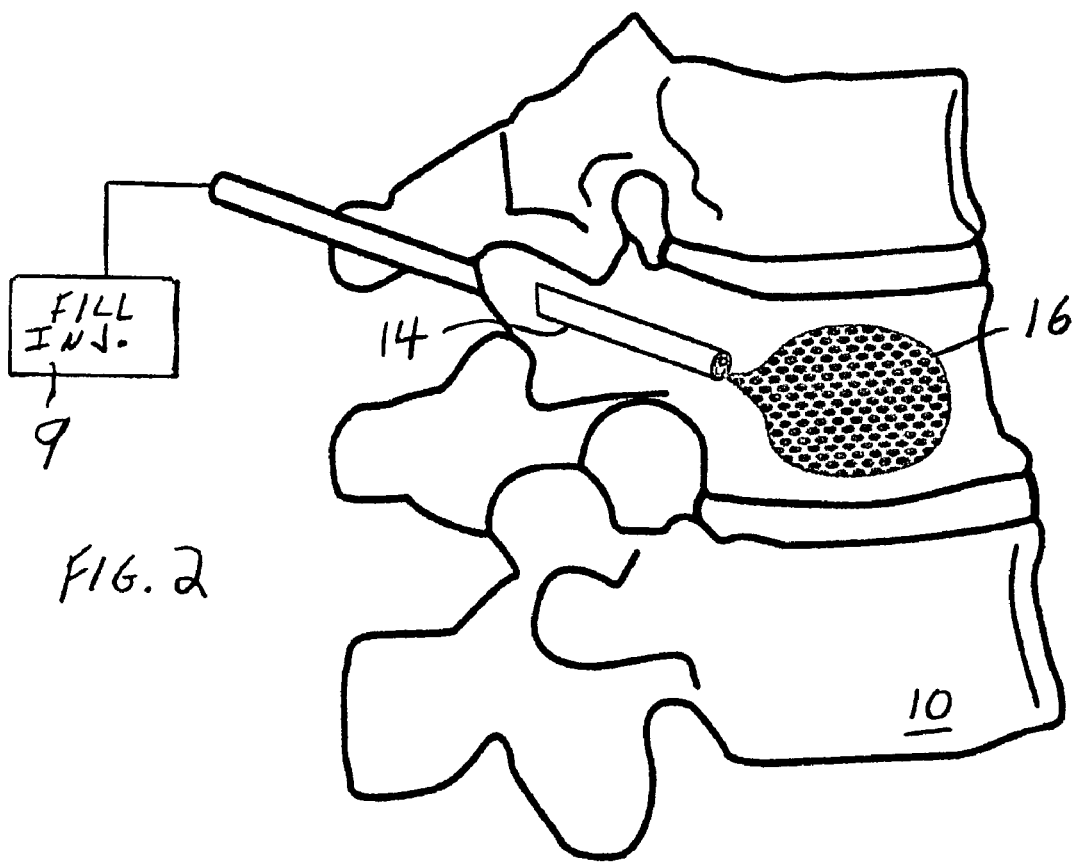
FIG. 2 schematically illustrates part of a spinal column with a cavity into which a mesh bag had been introduced via an injecting tube to inject a light-activated fill into the bag.

Either of the tubes can be used for endoscopic viewing of the procedure when the other tube is in use. FIG. 2 illustrates the spinal fill (not shown) being injected from a suitable supply 9 via one of the tubes 18, 20 into the bag 16 to fill same and such that it fills the space alongside the fracture such that when hardened the fractured region is reinforced by the hardened self-polymerized fill.

Figure 3:
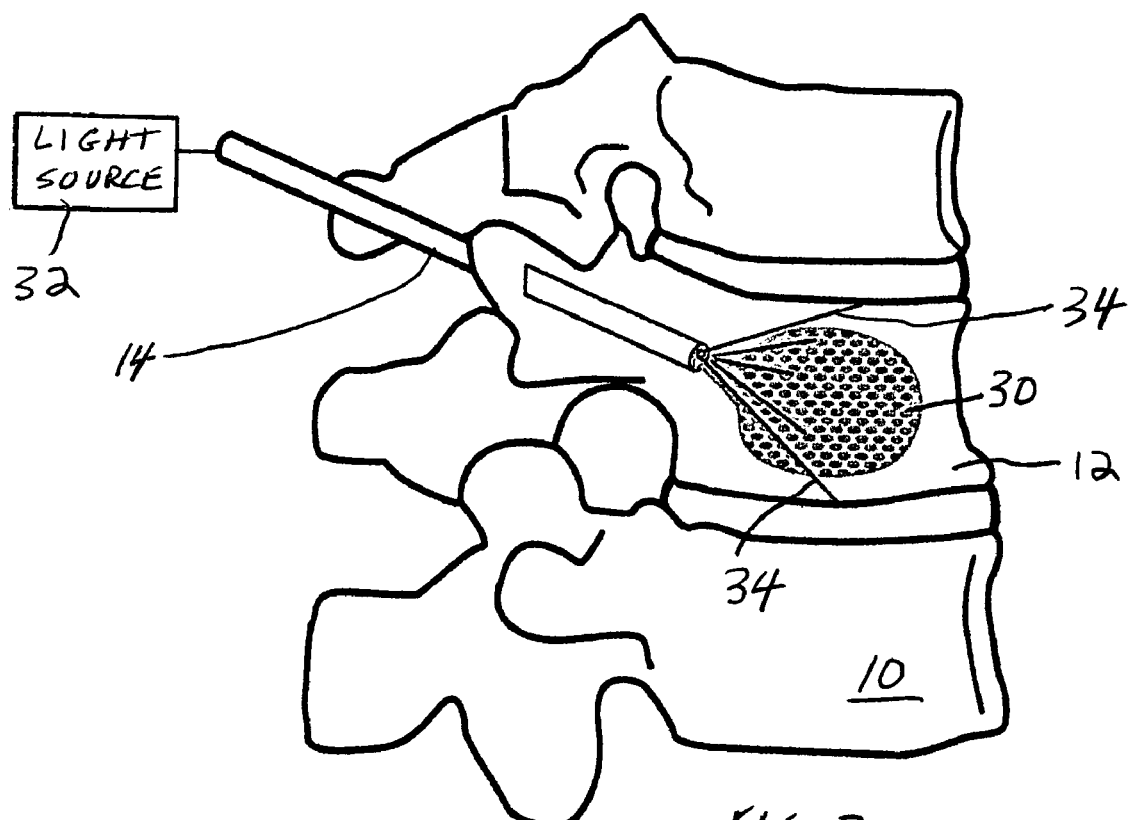
FIG. 3 schematically illustrates a following step in the procedure illustrated in FIG. 2 in which the injecting tube can be used for illuminating the injected fill with activating light.

When a light-activated fill is employed, then after the fill has been introduced directly to the surgical site or administered into the mesh bag, it must be illuminated with activating light to polymerize. Preferably, a mesh bag 30 composed of optical fibers is used to help distribute the light around the fill. This embodiment is illustrated in FIG. 3, which shows activating light being introduced via one of the inner tubes 18, 20 of the cannula 14. A suitable source is schematically illustrated at 32, the irradiating light by 34. In the alternative illustrated in FIG. 4, the activating light 36 is shown being introduced directly to a filled cavity or into the mesh bag (not shown) via the space 22 between the inner 15 and outer 14 tubes.

In this embodiment, the activating light is provided at the proximal end of the tube outside of the body from, for example, an UV source 32 supplying radiation capable of polymerizing and curing the fill inside the bag. The radiation can be transmitted down the tube 18 by, for example, mirroring the inside surface of the tube, or by extending a bundle of optical fibers that are transparent to the activating radiation down the tube 18 to the vicinity of the mesh opening. To further spread the radiation as completely as possible around the fill inside the mesh bag, the mesh fibers are constructed of thin flexible optical fibers, which are capable of conveying the radiation throughout the bag meshes so that the fill is illuminated from all sides.

It will also be apparent to those skilled in this art that the invention should not be limited to the fill injecting or light injecting devices shown as other devices can readily be devised to perform the same function as will be appreciated by the person of ordinary skill in this art.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A procedure for surgically treating spinal disease of a patient, the disease being associated with a particular site at the patient's spine, comprising the steps:
   (i) providing access to the site at the patient's spine associated with the disease,
   (ii) providing a mixture of polymerizable materials comprising liquid monomer isobutylmethacrylate and powdered polyisobutylmethacrylate to form a flowable polymerizable material,
   (iii) applying the flowable polymerizable material to the site at the patient's spine associated with the disease to treat the disease when hardened, the flowable material upon curing in situ forming a hardened polyisobutylmethacrylate.

2. A procedure for surgically treating spinal disease of a patient as claimed in claim 1, wherein the mixture of polymerizable materials comprises powdered polyisobutylmethacrylate, and liquid monomer isobutylmethacrylatethe with the powder being present in a quantity sufficient to form a flowable creamy mass, the liquid monomer and the powdered polymer being thoroughly mixed together to form a creamy mass before being applied to the site at the patient's spine.

3. A procedure for surgically treating spinal disease of a patient as claimed in claim 2, wherein step (i) is carried out by introducing an instrument through a cannula in the patient to the site at the patient's spine and removing spinal material from the patient's spine to form a cavity, and step (iii) is carried out by introducing an instrument through a cannula in the patient to the cavity at the patient's spine and injecting the flowable material to fill the cavity.

4. A procedure for surgically treating spinal disease of a patient as claimed in claim 3, wherein step (i) is carried out by first introducing an instrument through a cannula in the patient to the site at the patient's spine and removing spinal material from the patient's spine to form the cavity and next by introducing a hollow mesh bag into the thus-formed cavity, and step (iii) is carried out by introducing an instrument through a cannula in the patient to the cavity at the patient's spine and injecting the flowable material to fill the hollow mesh bag.

5. A procedure for surgically treating spinal disease of a patient, the disease being associated with a particular site at the patient's spine, comprising the steps:
   (i) providing access to the site at the patient's spine associated with the disease,
   (ii) applying a flowable material to the site at the patient's spine associated with the disease to treat the disease, the flowable material comprising a mixture of polymerizable materials comprising powdered polyisobutylmethacrylate, and liquid monomer isobutylmethacrylatethe that upon being irradiated with UV radiation form a hardened acrylate,
   (iii) applying to the introduced flowable material through a cannula in the patient UV radiation sufficient to cure the mixture to form the hardened acrylate.

6. A procedure for surgically treating spinal disease of a patient as claimed in claim 5, wherein step (i) is carried out by introducing an instrument through a cannula in the patient to the site at the patient's spine and removing spinal material from the patient's spine to form a cavity, step (ii) is carried out by introducing an instrument through a cannula in the patient to the cavity at the patient's spine and introducing into the hollow region a mesh bag constituted of UV transmitting strands and next injecting the flowable material to fill the mesh bag, and step (iii) is carried out by introducing UV radiation through a light-transmitting instrument through a cannula in the patient to irradiate the mesh bag and the material inside the mesh bag to cause same to polymerize and harden.

7. A procedure as claimed in claim 6, wherein the cannula comprises two side-by-side internal tubes one of which is configured to transmit UV radiation.

8. A surgical instrument as claimed in claim 6, wherein the cannula comprises an inner tube separated by an internal space configured to transmit UV radiation.

* * * * *